United States Patent
Kirwan, Jr. et al.

(10) Patent No.: US 10,531,932 B2
(45) Date of Patent: Jan. 14, 2020

(54) TIP PROTECTOR FOR ELECTROSURGICAL FORCEPS

(71) Applicant: Kirwan Surgical Products LLC, Marshfield, MA (US)

(72) Inventors: Lawrence T. Kirwan, Jr., Kingston, MA (US); Chadwick J. Whitcher, South Weymouth, MA (US)

(73) Assignee: Kirwan Surgical Products LLC, Marshfield, MA (US)

( * ) Notice: Subject to any disclaimer, the term of this patent is extended or adjusted under 35 U.S.C. 154(b) by 655 days.

(21) Appl. No.: 14/964,695

(22) Filed: Dec. 10, 2015

(65) Prior Publication Data

US 2017/0165021 A1    Jun. 15, 2017

(51) Int. Cl.
*A61B 50/30* (2016.01)
*B33Y 50/02* (2015.01)
*B33Y 80/00* (2015.01)
*B29L 31/00* (2006.01)

(52) U.S. Cl.
CPC ............ *A61B 50/30* (2016.02); *B33Y 50/02* (2014.12); *B33Y 80/00* (2014.12); *B29L 2031/7546* (2013.01)

(58) Field of Classification Search
CPC ..... A61B 50/30; A61B 50/3001; A61B 50/20; A61B 50/22; A61B 18/1442; A61B 2018/1462; A61B 2090/038; A61B 2090/0801; A61B 90/08; A61B 2017/305; A61B 2017/30; A61B 2017/2829; A61B 17/0493; A61B 17/30; B65D 41/02; B26B 29/00; A45C 13/002; B29L 2031/7546

USPC ...... 206/363, 214, 571, 575; 220/23.8, 23.2; 606/211, 206, 205, 210; 294/16, 99.2
See application file for complete search history.

(56) References Cited

U.S. PATENT DOCUMENTS

| | | | | |
|---|---|---|---|---|
| 4,009,899 A | * | 3/1977 | Johnson | B25B 9/02 294/33 |
| 4,041,952 A | | 8/1977 | Morrison, Jr. et al. | |
| 4,659,128 A | * | 4/1987 | Dong | A47G 21/103 294/99.2 |
| 4,787,663 A | * | 11/1988 | Laramie | A47G 21/103 294/99.2 |
| 4,834,030 A | | 5/1989 | Moore | |
| 5,254,131 A | * | 10/1993 | Razi | A61B 17/30 606/208 |
| 5,423,814 A | | 6/1995 | Zhu et al. | |
| 5,630,821 A | * | 5/1997 | Klaas | A61F 2/1664 606/107 |
| 5,702,270 A | * | 12/1997 | Casica | H01R 13/72 24/339 |
| 6,524,325 B2 | | 2/2003 | Shaw | |
| 6,926,712 B2 | | 8/2005 | Phan | |
| 7,235,073 B2 | | 6/2007 | Levine et al. | |
| 8,020,909 B1 | * | 9/2011 | LaVaque | B25B 9/02 294/99.2 |

(Continued)

*Primary Examiner* — Robert Poon
(74) *Attorney, Agent, or Firm* — Verrill Dana, LLP

(57) ABSTRACT

A tip protector for electrosurgical forceps is provided. The tip protector includes two sleeves connected by a bridge spacer. Each sleeve fits over a respective forceps tine to protect the tips of the forceps. The bridge spacer is sufficiently rigid to maintain the spacing between the tips and prevent the tines from closing or opening. In this manner, the tips can be protected from damage and the tines can be protected against misalignment.

8 Claims, 3 Drawing Sheets

(56) References Cited

U.S. PATENT DOCUMENTS

| | | | |
|---|---|---|---|
| 2005/0067308 A1* | 3/2005 | Thompson | A61B 17/34 206/363 |
| 2005/0240177 A1 | 10/2005 | Tabermejo, Jr. et al. | |
| 2006/0021891 A1* | 2/2006 | Franer | A61B 17/34 206/363 |
| 2006/0079934 A1 | 4/2006 | Ogawa et al. | |
| 2007/0208341 A1* | 9/2007 | Kirwan | A61B 18/1442 606/51 |
| 2009/0012519 A1 | 1/2009 | Manrique et al. | |
| 2009/0054925 A1* | 2/2009 | Cho | A61B 17/30 606/210 |
| 2010/0001541 A1* | 1/2010 | Sugiyama | B25B 9/02 294/99.2 |

\* cited by examiner

TIP PROTECTOR FOR ELECTROSURGICAL FORCEPS

CROSS REFERENCE TO RELATED APPLICATIONS

N/A

STATEMENT REGARDING FEDERALLY SPONSORED RESEARCH OR DEVELOPMENT

N/A

BACKGROUND

Electrosurgical forceps have a pair of resilient blade members or tines that are used for grasping and coagulating tissue. The forceps can be bipolar or monopolar; thus, at least one of the tines is electrically conducting. The tips of the tines are aligned so that tissue can be grasped between opposing surfaces of the tips when a surgeon squeezes the tines together. Forceps can be disposable after a single use or reusable after re-sterilization.

SUMMARY OF THE INVENTION

The invention relates to a tip protector for electrosurgical forceps. During shipping or at other times, electrosurgical forceps can be subjected to movements or impacts sufficient to cause misalignment of the tines and/or damage to the tips. Accordingly, a tip protector is provided that can protect the tips from damage and hold the tines at a set spacing to prevent misalignment during shipping or at other times.

In one embodiment, the tip protector includes two sleeves connected by a bridge spacer. Each sleeve fits over a respective distal portion of a forceps tine such that the tips of the forceps are retained within the sleeves. The bridge spacer is sufficiently rigid to maintain a set spacing between the tines and prevent the tines from closing or opening beyond the set spacing. In this manner, the tips can be protected from damage and the tines can be protected against becoming misaligned.

Other aspects of the method and system include the following:

1. A tip protector for electrosurgical forceps, the electrosurgical forceps comprising a pair of tines connected at a proximal end to an insulating cap, each tine having a length extending from the insulating cap to a tip, the tips of the tines configured for gripping tissue between opposed surfaces of the tips, at least a distal portion of each tine tapered from a wider section to a narrower section at the tip such that the tip is narrower than the wider section, the tip protector comprising:
   a pair of sleeves, each sleeve comprising:
      an elongated cylindrical configuration extending from a proximal end to a distal end,
      an opening at the proximal end,
      a channel within each sleeve extending from the opening at the proximal end toward the distal end,
      the channel having a length sized to receive the distal portion of one of the tines of the electrosurgical forceps, and
      the opening having a circumference sized to be larger than a circumference of the tip and sized to form a friction fit with the distal portion of the tine at a location spaced from the tip; and
   a bridge spacer extending between and connecting the sleeves at the proximal ends of each sleeve, wherein the bridge spacer is rigid to maintain the sleeves in parallel and at a set spacing.

2. The tip protector of item 1, wherein the sleeves are parallel to each other and the bridge spacer extends transversely between the parallel sleeves.

3. The tip protector of item 2, wherein the bridge spacer includes first and second faces extending between the sleeves, and wherein a gripping feature is formed on one or both of the first and second faces.

4. The tip protector of item 3, wherein the gripping feature comprises a rib, a pair of ribs, a rough texture, or a fingertip recess.

5. The tip protector of any of items 1-4, wherein the proximal end has an inner circumference selected to frictionally engage the tine at the wider section spaced from the tip.

6. The tip protector of any of items 1-5, each sleeve further including an opening at the distal end, the channel extending from the opening at the proximal end to the opening at the distal end.

7. The tip protector of any of items 1-6, wherein the pair of sleeves and the bridge spacer are integral and formed of a same material.

8. The tip protector of any of items 1-7, wherein the tip protector comprises a material that is able to withstand gamma radiation sterilization.

9. The tip protector of any of items 1-8, wherein the tip protector comprises a material selected from the group consisting of a polyvinyl chloride, a nylon, a polyvinylidene difluoride, a polypropylene, a low density polyethylene, a high density polyethylene, a thermoplastic elastomer, a thermoplastic vulcanizate, a silicone, an acrylonitrile-butadiene-styrene, and a polylactic acid.

10. A computer-readable medium storing instructions that, when executed by at least one processor of an additive manufacturing device, cause the additive manufacturing device to generate a three-dimensional object comprising the tip protector of any of items 1-9.

DESCRIPTION OF THE DRAWINGS

The invention will be more fully understood from the following detailed description taken in conjunction with the accompanying drawings in which.

DETAILED DESCRIPTION OF THE INVENTION

Figure 1:
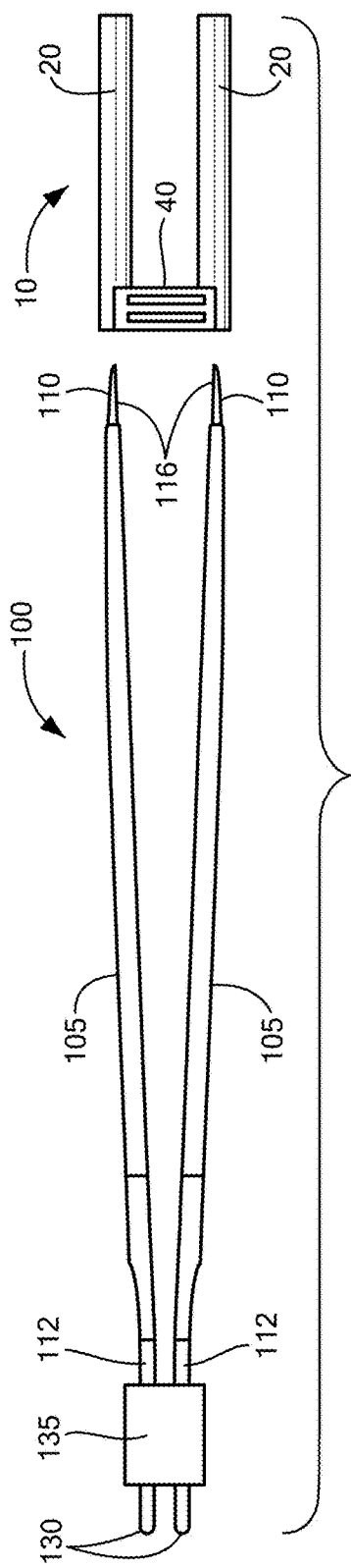
FIG. 1 is an exploded view of an electrosurgical forceps with an embodiment of a tip protector.
Figure 2:
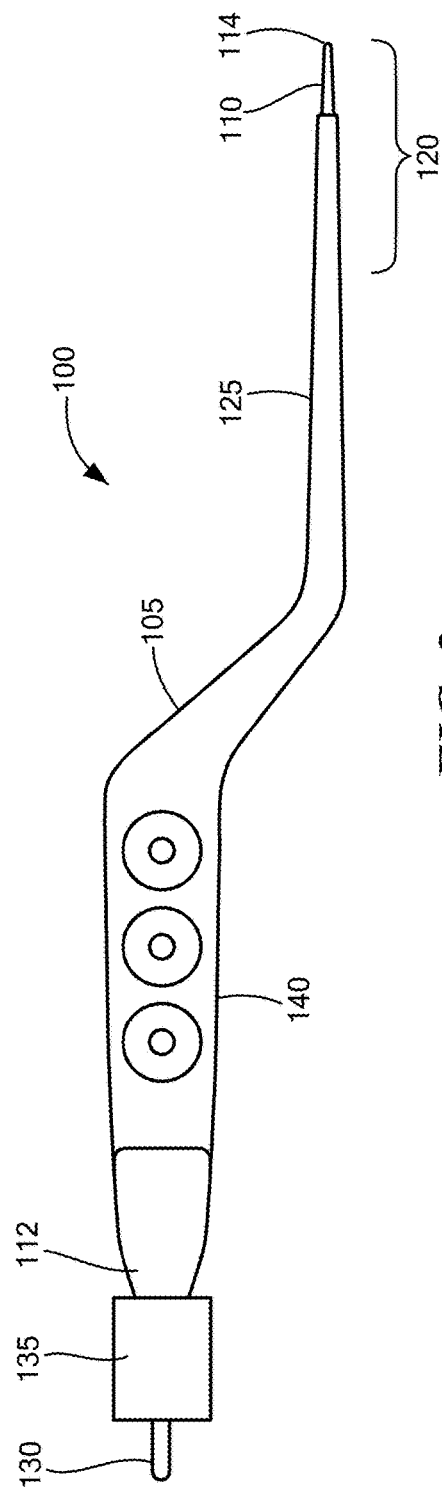
FIG. 2 is a plan view of the electrosurgical forceps of FIG. 1.
Figure 3:
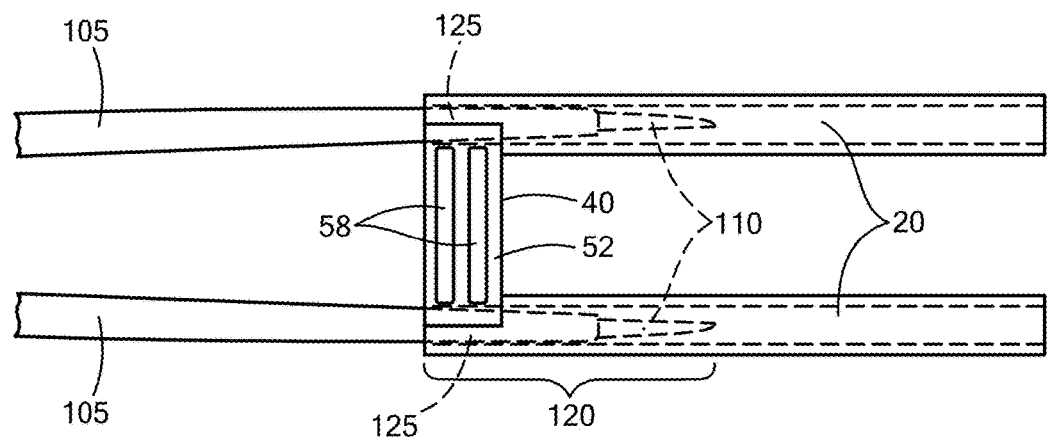
FIG. 3 is a partial view of the tip protector installed on an electrosurgical forceps of FIG. 1.

One embodiment of a tip protector 10 is illustrated in conjunction with an electrosurgical forceps 100 in FIGS. 1-3. The tip protector includes two parallel sleeves 20 connected by a transverse bridge spacer 40. Each sleeve fits over a respective distal portion of a forceps tine 105 such that the tip 110 of the forceps 100 is retained within the sleeve. The bridge spacer is sufficiently rigid to maintain a set spacing between the tines and prevent the tines from closing or opening beyond the set spacing. In this manner, the tips can be protected from damage and the tines can be protected against becoming misaligned.

Referring to FIGS. 1 and 2, a typical electrosurgical forceps 100 has first and second resilient blades or tines 105, at least one of which serves as an electrode. Each of the tines is elongated and extends from a first or proximal end 112 to a second or distal end 114 at the tip 110. The tines are generally flat, and the tips are configured for gripping tissue between opposed surfaces 116. At least a distal portion 120 of each tine 105 is tapered from a wider section 125 to the distal end 114 at the tip 110, such that the tip is narrower than the wider section. (See FIG. 2.) The first ends 112 are electrically connected in any suitable manner, such as by crimping, welding, or soldering, to terminal pins 130. The first ends 112 along with the terminal pins 130 are encapsulated using an epoxy-based material or otherwise mounted within an insulating cap 135. In some embodiments, the tines can be insulated with an insulating material along most of their length from the cap to a location close to the tip. In other embodiments, the tines can be uninsulated. A plating of an electrically and thermally conductive biocompatible material such as gold may be provided on the tip of an insulated tine, or over the tip or the entire body of an uninsulated tine. In use, a physician grasps the resilient tines at a region 140 between the cap 135 and the tips 110 and squeezes the tines to close the tips over a section of tissue.

Figure 4:
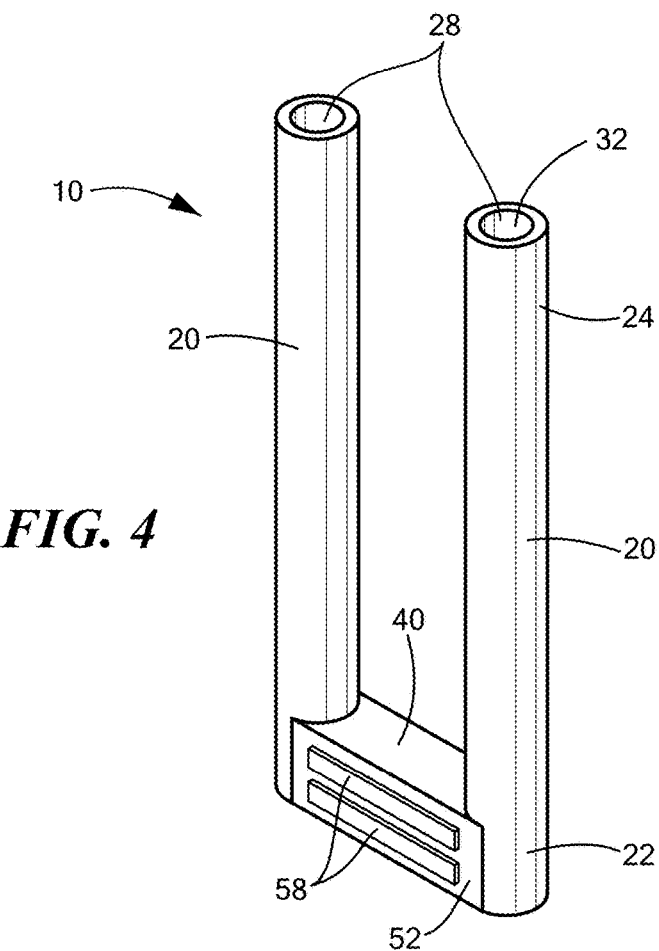
FIG. 4 is an isometric view of an embodiment of a tip protector for electrosurgical forceps.
Figure 5:
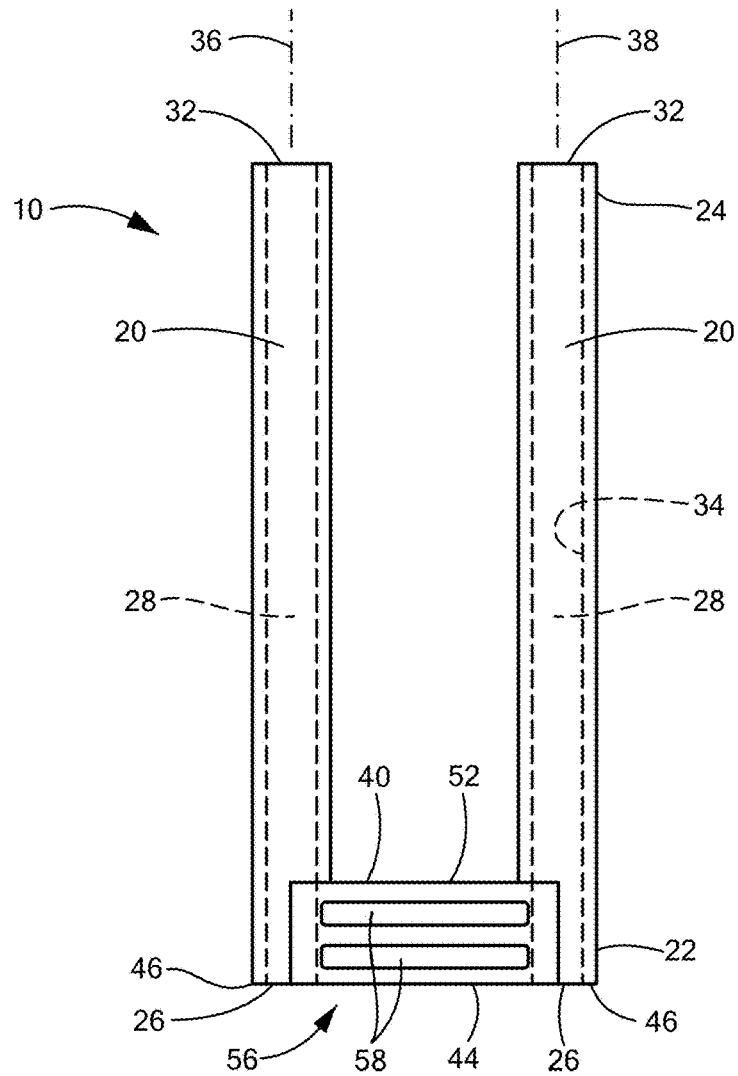
FIG. 5 is a front plan view of the tip protector of FIG. 4.
Figure 6:
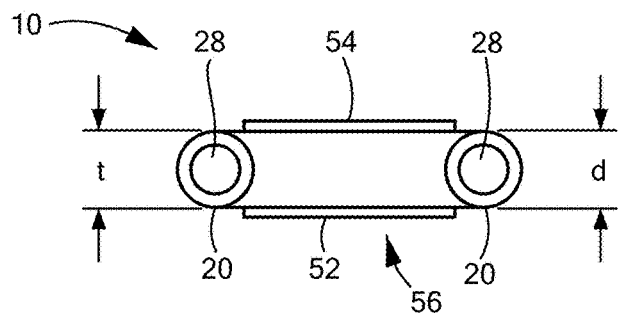
FIG. 6 is a top view of the tip protector of FIG. 4.

One embodiment of a tip protector 10 for such electrosurgical forceps is described more particularly with reference to FIGS. 4-6. Each sleeve 20 has an elongated cylindrical configuration extending from a proximal end 22 to a distal end 24. An opening 26 is provided at the proximal end. A channel 28 within each sleeve extends from the opening at the proximal end toward the distal end. In some embodiments, an opening 32 can be provided in the distal end 24 as well, such that the channel extends entirely through the length of the sleeve.

The channel 28 has a length sized to receive the distal portion 120 of one of the tines 105 of the electrosurgical forceps 100 and can have a cylindrical configuration along its length defined by the circumference of an interior surface 34 of the sleeve 20. The opening 26 at the proximal end 22 has a circumference sized to be larger than a circumference of the tip so that the tip can be readily inserted through the opening into the channel. The inner circumference of the proximal end at or near the opening 26 is also sized to form a friction fit with the wider section 125 of the distal portion 120 of the tine at a location spaced from the tip 110. As noted above, at least the distal portion 120 of each tine of the electrosurgical forceps is tapered along its length from the wider section 125 spaced from the tip to a narrower section at the tip. Thus, as the tine is inserted into the channel, eventually a section of the tine that is sufficiently wide frictionally engages the interior surface 34 of the channel at or adjacent the proximal opening 26. In this manner, the tip protector 10 can be frictionally retained on the forceps 100 with the tips 110 located within the sleeves 20 at a location between the proximal ends 22 and the distal ends 24. In the embodiment shown in FIG. 3, the tips are retained generally midway along the sleeve.

The bridge spacer 40 extends transversely between the proximal ends 22 of the sleeves 20 to connect the sleeves in parallel alignment. The length of the bridge spacer can be selected to maintain the sleeves 20, and thus the forceps tines 105, at a set spacing. The bridge spacer is formed to be sufficiently rigid to maintain the sleeves in parallel and at the set spacing. For example, the bridge spacer can be formed from a material with a sufficient hardness such that the bridge spacer will not bend, flex, compress, or extend to significantly alter the set spacing. In some embodiments, the bridge spacer should not move more than ±0.01 inch. In some embodiments, the bridge spacer has a hardness of at least about 75 Shore A durometer.

In the embodiment illustrated in FIGS. 4-6, the bridge spacer 40 has a generally rectangular cross section in a plane parallel to the axial extent of the sleeves (indicated by axes 36, 38) and has a thickness dimension t that is approximately the same as the exterior diameter d of each of the sleeves 20. The bridge spacer 40 has a proximal surface 44 coextensive with surfaces 46 at the proximal ends 28 of the sleeves 20. The bridge spacer includes a first face 52 and a second face 54 extending in parallel between the sleeves. A user can grasp the tip protector at the first and second faces when placing the tip protector on the forceps or removing the tip protector from the forceps. The first and second faces 52, 54 can include a gripping feature 56 thereon to facilitate grasping by the user. The gripping feature can include, for example, one or more protruding ribs 58 on each face, a rough texture, a recess to receive a fingertip, and the like.

It will be appreciated that the sleeves 20 can have a slightly tapered or conical configuration on either or both of the interior surface or the exterior surface without departing from the ability to protect the tips and maintain the tine spacing. Similarly, the sleeves can be slightly curved or offset from parallel without departing from the ability to protect the tips and maintain the tine spacing. The bridge spacer 40 can likewise have other configurations than the rectangular configuration shown in FIGS. 4-6.

The tip protector 10 can be manufactured in any suitable manner. In some embodiments, the tip protector can be manufactured by injection molding. In other embodiments, the sleeves can be separately extruded and then overmolded with the bridge spacer. In some embodiments, the sleeves and the bridge spacer of the tip protector can be integral and formed of a same material. In other embodiments, the sleeves and the bridge spacer can be formed separately and subsequently joined together, either of a same material or of different materials.

The tip protector can be made using various additive manufacturing or 3D printing processes, such as stereolithography, fused deposition, selective sintering with heat or laser, and the like, in which a product is fabricated layer by layer. For example, a three-dimensional design of the product can be generated, for example, using any suitable computer aided design system or from a scan of the product. The three-dimensional data can be converted into a stereolithographic or STL file or other suitable file format that can be further processed to produce a data file of two-dimensional slices suitable for use by an additive manufacturing device to generate a three-dimensional object layer by layer.

The tip protector can be made of any suitable medical grade material or materials. Exemplary materials include, without limitation, a polyvinyl chloride (PVC), a nylon, a polyvinylidene difluoride (PVDF), a polypropylene, a low density polyethylene (LDPE), a high density polyethylene (HDPE), a thermoplastic elastomers such as a thermoplastic vulcanizate (TPV), a silicone, an acrylonitrile-butadiene-styrene (ABS), or a polylactic acid (PLA).

In some embodiments, the tip protector can be made from a material that can withstand sterilization by gamma radiation. For example, after manufacturing, the forceps, particularly disposable, single-use forceps, can be fitted with a tip protector, sealed in a package, and subjected to gamma radiation for sterilization. Reusable forceps can also be fitted with a tip protector during sterilization using sterilization methods that do not require forceps surfaces to be exposed, such as sterilization with gamma radiation.

The tip protectors can be used during storage and transportation of the forceps. The forceps are particularly prone to misalignment during shipping. However, the tip protector can be used at other times as well.

As used herein, "consisting essentially of" allows the inclusion of materials or steps that do not materially affect the basic and novel characteristics of the claim. Any recitation herein of the term "comprising", particularly in a description of components of a composition or in a description of elements of a device, can be exchanged with "consisting essentially of" or "consisting of".

It will be appreciated that the various features of the embodiments described herein can be combined in a variety of ways. For example, a feature described in conjunction with one embodiment may be included in another embodiment even if not explicitly described in conjunction with that embodiment.

The present invention has been described in conjunction with certain preferred embodiments. It is to be understood that the invention is not limited to the exact details of construction, operation, exact materials or embodiments shown and described, and that various modifications, substitutions of equivalents, alterations to the compositions, and other changes to the embodiments disclosed herein will be apparent to one of skill in the art.

What is claimed is:

1. Electrosurgical forceps having a tip protector, comprising:
    electrosurgical forceps comprising a pair of tines connected at a proximal end to an insulating cap, each tine having a length extending from the insulating cap to a tip, the tips of the tines configured for gripping tissue between opposed surfaces of the tips, at least a distal portion of each tine tapered from a wider section to a narrower section at the tip such that the tip is narrower than the wider section; and
    a tip protector comprising:
    a pair of sleeves, each sleeve comprising:
        an elongated cylindrical configuration extending from a proximal end of the sleeve to a distal end of the sleeve,
        an opening at the proximal end of the sleeve, and an opening at the distal end of the sleeve,
        a channel within each sleeve extending from the opening at the proximal end of the sleeve to the opening at the distal end of the sleeve,
        the channel having a length sized to receive the distal portion of one of the tines of the electrosurgical forceps with the tip of the tine retained within the sleeve between the proximal end of the sleeve and the distal end, and
        the opening having a circumference sized to be larger than a circumference of the tip and sized to form a friction fit with the distal portion of the tine at a location spaced from the tip; and
    a bridge spacer extending between and connecting the sleeves at the proximal ends of each sleeve, wherein the bridge spacer is rigid to maintain the sleeves in parallel alignment and at a set spacing.

2. The electrosurgical forceps having the tip protector of claim 1, wherein the sleeves are parallel to each other and the bridge spacer extends transversely between the sleeves.

3. The electrosurgical forceps having the tip protector of claim 2, wherein the bridge spacer includes first and second faces extending between the sleeves, and wherein a gripping feature is formed on one or both of the first and second faces.

4. The electrosurgical forceps having the tip protector of claim 3, wherein the gripping feature comprises a rib, a pair of ribs, a rough texture, or a fingertip recess.

5. The electrosurgical forceps having the tip protector of claim 1, wherein the proximal end of each sleeve has an inner circumference selected to frictionally engage the tine at the wider section spaced from the tip.

6. The electrosurgical forceps having the tip protector of claim 1, wherein the pair of sleeves and the bridge spacer are integral and formed of a same material.

7. The electrosurgical forceps having the tip protector of claim 1, wherein the tip protector comprises a material that can be subjected to gamma radiation sterilization.

8. The electrosurgical forceps having the tip protector of claim 1, wherein the tip protector comprises a material selected from the group consisting of a polyvinyl chloride, a nylon, a polyvinylidene difluoride, a polypropylene, a low density polyethylene, a high density polyethylene, a thermoplastic elastomer, a thermoplastic vulcanizate, a silicone, an acrylonitrile-butadiene-styrene, and a polylactic acid.

* * * * *